United States Patent [19]

Uchiumi et al.

[11] Patent Number: 4,518,793

[45] Date of Patent: May 21, 1985

[54] PREPARATION OF ACETONE DICARBOXYLIC ACID DIESTERS

[75] Inventors: Shinichiro Uchiumi; Kikuo Ataka, both of Ube, Japan

[73] Assignee: UBE Industries, Ltd., Ube, Japan

[21] Appl. No.: 542,356

[22] Filed: Oct. 17, 1983

[30] Foreign Application Priority Data

Oct. 26, 1982 [JP]  Japan ................ 57-186686

[51] Int. Cl.$^3$ .................. C07C 67/02; C07C 67/36; C07C 67/38; C07C 69/716
[52] U.S. Cl. ........................ 560/175; 560/176
[58] Field of Search ................ 560/175, 176

[56] References Cited

U.S. PATENT DOCUMENTS 3,773,821  11/1973  Broussard ............... 560/176
4,229,589  10/1980  Nishimura et al. ....... 560/204
4,229,591  10/1980  Nishimura et al. ....... 560/204

Primary Examiner—Vivian Garner
Attorney, Agent, or Firm—Frishauf, Holtz, Goodman & Woodward

[57]  ABSTRACT

Disclosed is a process for preparing an acetone dicarboxylic acid diester, which comprises allowing diketene, carbon monoxide and a nitrous acid ester to react in the presence of a palladium halide or a complex thereof.

22 Claims, No Drawings

PREPARATION OF ACETONE DICARBOXYLIC ACID DIESTERS

This invention relates to a novel process for preparing acetone dicarboxylic acid diester. In the art, acetone dicarboxylic acid diester is also sometimes called as 3-oxoglutaric acid diester.

Acetone dicarboxylic acid diester is a useful compound as an intermediate for synthesis of fine chemicals such as pharmaceuticals, agricultural medicines, etc.

In the prior art, various processes have been proposed for preparation of acetone dicarboxylic acid diester.

A representative process among them comprises oxidizing citric acid with fuming sulfuric acid to form acetone dicarboxylic acid and then esterifying acetone dicarboxylic acid to prepare acetone dicarboxylic acid diester. However, according to this process, acetone dicarboxylic acid which is the intermediate product is an unstable material and will readily be decomposed with hot water, an acid or an alkali into acetone and carbon dioxide. Therefore, its esterification is not feasible in industrial application, involving drawbacks of poor yield and selectivity of the desired product of acetone dicarboxylic acid diester. For example, as the process for esterification of acetone dicarboxylic acid, there may be mentioned the process in which dry hydrogen chloride gas is blown into an alcoholic solution of acetone dicarboxylic acid (Org. Synth. Coll. Vol. 1, 237) or the process in which an alcohol is added to acetone dicarboxylic acid liquor as the product oxidized with fuming sulfuric acid [J. Org. Chem. 22, 1385, (1957)]. The yields according to these processes from citric acid, however, are as low as 30 to 60%.

As other processes for preparation of acetone dicarboxylic acid diester, there may be included the process in which citric acid diester is oxidized with chromium oxide (U.S. Pat. No. 2,848,480); the process in which citric acid diester is oxidized with fuming sulfuric acid [J. Org. Chem., 22, 1385, (1957)]; and further the process in which citric acid is decomposed with sulfuric acid to be esterified (Japanese Unexamined Patent Publication No. 63943/1981). However, none of these processes are industrially advantageous, since it is required to use an industrially intractable material such as fuming sulfuric acid or a chromium compound or it is required to control severely the reaction conditions because of great changes in yield or selectively of the desired product depending on the reaction conditions.

In view of the state of the art as mentioned above, the present inventors have made various studies in order to develop an industrially excellent process for preparation of acetone dicarboxylic acid diester. As a consequence, it has now been found that the above object can be accomplished by allowing diketene, carbon monoxide and a nitrous acid ester to react with each other in the presence of a catalyst comprising a palladium halide or its complex to produce acetone dicarboxylic acid diester industrially advantageously. This invention has been accomplished on the basis of such a finding.

The reaction in this invention is an entirely new reaction and proceeds according to the following reaction scheme:

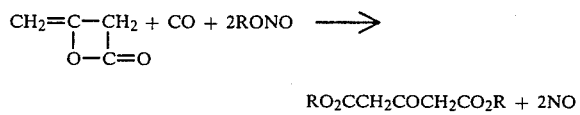

$$RO_2CCH_2COCH_2CO_2R + 2NO$$

wherein R represents an alkyl group or a cycloalkyl group.

The nitrous acid ester to be used in the process of this invention is an ester of a saturated monohydric aliphatic alcohol having 1 to 8 carbon atoms or alicyclic alcohol with nitrous acid. As the alcoholic component, there may be employed aliphatic alcohols such as methanol, ethanol, n-(and iso-)propanol, n-(iso-, sec-, tert-)butanol, n-(and iso-)amyl alcohol, hexanol, octanol and alicyclic alcohols such as cyclohexanol, methyl cyclohexanol, and the like. These alcohols may also contain substituents which do not interefere with the reaction such as alkoxy groups.

The nitrous acid ester to be used in this reaction is not necessarily required to be in the form of a nitrous acid ester, but there may be employed the starting materials which can form a nitrous acid in situ in the reaction system. That is, in place of a nitrous acid ester, it is also useful to employ an alcohol with a nitrogen oxide selected from nitrogen monoxide, nitrogen dioxide, dinitrogen trioxide and dinitrogen tetraoxide or a hydrated product thereof, optionally with introduction of a molecular oxygen-containing gas. As the hydrated product of nitrogen oxide, nitric acid or nitrous acid may effectively be used. In these cases, the alcohol provided for use is selected from the alcoholic components which are constituents of the nitrous acid esters as mentioned above.

A nitrous acid ester, when it is gaseous at normal temperature, can be fed as a gas, or as a liquid when it is liquid at normal temperature, directly into the reaction system, or accompanied with carbon monoxide, or even as a solution dissolved in a solvent which does not interfere with the reaction. Sometimes, its total amount can be placed in the system before the reaction. The nitrous acid ester is required to be used in an amount of 2-fold moles or more of diketene, but preferably 2 to 50 moles per mole of diketene in ordinary case, or 2 to 100 moles per mole of diketene in case a low boiling nitrous acid ester is used. Diketene to be employed may be either pure or contain impurities, but it is preferred to purify diketene before use when it contains an impurity having a deleterious effect on the reaction. Diketene can be charged at once in the system before the reaction, but it is desirable for the purpose of suppressing side reactions to feed diketene by injecting into the reaction system during the reaction. The concentration of diketene in the reaction system may preferably be maintained at the range from 0.1 to 30 wt.%, because side reactions are liable to occur at too high a concentration, while the progress of the reaction is retarded at too low a concentration.

The palladium halide in this invention may include palladium halide compounds such as palladium chloride, palladium bromide, palladium iodide and the like. As their palladium complexes, there may be included, for example, complexes represented by the formula: $PdX_2(L\text{-}CN)_2$ (wherein X represents a halogen atom and L represents an alkyl group having 1 to 20 carbon atoms or a phenyl group), complexes represented by the formula: $M_2PdX_4$ (wherein M represents an alkali metal and X represents a halogen atom) or complexes represented by the formula: [PdCl$_2$(olefin)]$_n$ (wherein an olefin having 2 to 20 carbon atoms is useful and n is 1 or 2). These palladium catalysts may also be carried on inert carriers, as exemplified by activated charcoal, silicon carbide, alumina, silica, diatomaceous earth, pumice stone, zeolite, magnesium oxide, titanium oxide, molecular sieve, etc. A palladium halide or its complex may be used at a level of its concentration in the reaction system generally of 1 ppm to 5 wt.%, preferably 10 ppm to 0.5 wt.%, calculated on the basis of palladium metal.

The reaction can be accelerated by adding copper salts such as $CuCl_2$, $CuCl$, $Cu(NO_3)_2$, $CuBr_2$ and $CuBr$ to the above catalyst system. Amount of the copper salts may be 0.1 to 10 moles per mole of palladium halide.

In the reaction of this invention, the rate of formation of the desired product and its selectivity can further be enhanced by permitting an appropriate amount of an alcohol to exist in the reaction system.

The alcohol to be used for this purpose may be chosen from the alcoholic components which are constituents of the above-mentioned nitrous acid esters, and its amount may be 20 moles or less, preferably 0.1 to 10 moles per mole of diketene.

The reaction of this invention may be carried out also in gas phase, but it is generally practiced in liquid phase. As the solvent to be used in a liquid phase reaction, it is preferred to use a non-protonic solvent such as acetonitrile, propionitrile, benzonitrile, dioxane, tetrahydrofuran, diethylether, dibutylether, chlorobenzene, nitrobenzene, dimethylformamide, dimethyl sulfoxide, nitromethane, acetone, etc.

The amount of carbon monoxide employed is not particularly limited, but the more its amount is, the more advantageous effect can be obtained on the reaction. Its partial pressure is generally 0.01 to 100 atm., preferably 0.1 to 5 atm. in order for the process to be industrially advantageous.

The reaction may be carried out at a temperature from $-10°$ to 250° C., preferably from 15° to 150° C. The reaction may also be conducted in a closed system by use of an autoclave or other means. However, since nitrogen monoxide is generated as can be seen from the above reaction scheme, it is industrially desirable to practice the reaction according a flow system, while removing the nitrogen monoxide generated.

The present invention is illustrated by referring to the following Examples. In each of the Examples, the reaction product was identified by measurement of IR absorption spectrum, NMR spectrum (proton carbon-13) and Mass spectrum and comparison with standard sample.

EXAMPLE 1

To 50 ml of dioxane were added 0.355 g (2.0 mmol) of palladium chloride and 5.75 g (64.8 mmol) of diketene, and, while stirring the mixture at room temperature, a gas mixture of methyl nitrite, carbon monoxide and methanol was blown thereinto at gas flow rates of 0.1 mol/hr. for methyl nitrite, 190 ml/min. for carbon monoxide and 10 ml/min. for methanol, respectively, for 2.5 hours. The reaction product was quantitatively analyzed by gas chromatography to confirm that 3.51 g (20.2 mmol) of dimethyl acetone dicarboxylate was formed.

EXAMPLE 2

An experiment was conducted according to the same procedure as in Example 1 except for using 383 mg (1 mmol) of PdCl$_2$(C$_6$H$_5$CN)$_2$ in place of palladium chloride as the catalyst. As the result, 3.17 g (18.2 mmol) of dimethyl acetone dicarboxylate was observed to be formed.

EXAMPLE 3

An experiment was conducted according to the same procedure as in Example 2 except for carrying out the reaction under pressurization of 2 atm. (guage) of carbon monoxide. As the result, 1.26 g (7.24 mmol) of dimethyl acetone dicarboxylate was observed to be formed.

EXAMPLE 4

An experiment was conducted according to the same procedure as in Example 2 except that no diketene was initially charged but it was added dropwise as a 20 wt.% dioxane solution over 2 hours into the reaction system. As the result, 3.25 g (18.7 mmol) of dimethyl acetone dicarboxylate was observed to be formed.

EXAMPLE 5

To 35 ml of acetonitrile was added 1.0 mmol of palladium chloride and the mixture was heated to 70° C. to prepare a homogenous solution, followed by addition of 5 ml of 20 wt.% diketene solution in acetonitrile. Subsequently, while maintaining the reaction mixture at 70° C. and blowing, a gas mixture of methyl nitrite, carbon monoxide and methanol was blown thereinto at gas flow rates of 40 ml/min. for methyl nitrite, 360 ml/min. for carbon monoxide and 20 ml/min. for methanol, respectively, 58 ml of a 20 wt.% diketene solution in acetonitrile was added over 2 hours. Then, blowing of the above gas mixure was further continued for 2 hours. The reaction product was quantitatively analyzed by gas chromatography. The results are shown in Table 1.

EXAMPLE 6

An experiment was conducted according to the same procedure as in Example 5 except for using 1 mmol of PdCl$_2$(CH$_3$CN)$_2$ in place of palladium chloride as the catalyst. The results are shown in Table 1.

EXAMPLE 7

An experiment was conducted according to the same procedure as in Example 5 except for changing the amount of palladium chloride employed to 0.50 mmol, changing the concentration of the acetonitrile solution of diketene added dropwise over 2 hours during the reaction to 31 wt.% and its amount to 50 ml, and further changing the time for blowing the gas mixture of methyl nitrite, carbon monoxide and methanol after the dropwise addition of the solution to 3 hours. The results are shown in Table 1.

EXAMPLE 8

An experiment was conducted according to the same procedure as in Example 7 except for changing the amount of palladium chloride employed to 0.31 mmol. The results are shown in Table 1.

TABLE 1

| Example | Catalyst (amount, mmol) | Diketene Amount used (mmol) | Conversion (%) | Dimethyl acetone dicarboxylate formed Amount (mmol) | Selectivity* (%) |
|---|---|---|---|---|---|
| 5 | PdCl$_2$ (1.0) | 108 | 100 | 73.2 | 62.9 |
| 6 | PdCl$_2$(CH$_3$CN)$_2$ (1.0) | " | " | 72.4 | 67.7 |
| 7 | PdCl$_2$ (0.5) | 148 | 97 | 75.2 | 52.4 |
| 8 | PdCl$_2$ (0.31) | " | 70 | 66.6 | 64.9 |

*based on diketene

EXAMPLE 9

An experiment was conducted according to the same procedure as in Example 5 except for using 0.50 mmol of palladium bromide in place of palladium chloride as the catalyst. As the result, 25.1 mmol of dimethyl acetone dicarboxylate was obtained.

EXAMPLE 10

To 35 ml of acetonitrile was added 1.0 mmol of palladium chloride and the mixture was heated to 70° C. to prepare a homogeneous solution, followed by addition of 5 ml of 20 wt.% diketene solution in acetonitrile. Subsequently, while maintaining the reaction mixture at 70° C. and blowing, a gas mixture of ethyl nitrite, carbon monoxide and ethanol was blown thereinto at gas flow rates of 40 ml/min. for ethyl nitrite, 374 ml/min. for carbon monoxide and 6 ml/min. for ethanol, respectively, 50 ml of a 27.5 wt.% diketene solution in acetonitrile was added over 2 hours. Then, blowing of the above gas mixure was further continued for 2 hours. The reaction product was quantitatively analyzed by gas chromatography. The results are shown in Table 2.

EXAMPLE 11

An experiment was conducted according to the same procedure as in Example 10 except for using 1 mmol of PdCl$_2$(CH$_3$CN)$_2$ in place of palladium chloride as the catalyst. The results are shown in Table 2.

TABLE 2

| Example | Catalyst (amount, mmol) | Diketene Amount used (mmol) | Conversion (%) | Diethyl acetone dicarboxylate formed Amount (mmol) | Selectivity* (%) |
|---|---|---|---|---|---|
| 10 | PdCl$_2$ (1.0) | 131 | 40 | 34.1 | 65.0 |
| 11 | PdCl$_2$(CH$_3$CN)$_2$ (1.0) | " | 40 | 34.6 | 66.4 |

*based on diketene

EXAMPLE 12

To 35 ml of acetonitrile was added 260 mg (1.0 mmol) of PdCl$_2$(CH$_3$CN)$_2$, and the mixture was maintained by heating at 70° C. Then, while blowing carbon monoxide at the rate of 380 ml/min., a mixture of 26.6 g (258 mmol) of n-butyl nitrite, 10.84 g (129 mmol) of diketene and 20 ml of acetonitrile was added over 2 hours, followed further by blowing of carbon monoxide for additional 1.5 hours. As the result of quantitative determination of the reaction product isolated by distillation, 0.62 g (2.4 mmol) of n-butyl acetone dicarboxylate was confirmed to be formed.

EXAMPLE 13

An experiment was conducted according to the same procedure as in Example 7 except that a gas mixture of methyl nitrite and carbon monoxide containing no methanol was passed through the reaction mixture. As the result, 25.7 mmol of dimethyl acetone dicarboxylate was found to be formed with a diketene conversion of 69%, with its selectivity being 25%.

EXAMPLE 14

A mixture of palladium chloride (2.85 mmol) and acetonitrile (300 mmol) was heated to 50° C. while stirring to make a homogeneous solution, into which a gas mixture of 15% (v/v) methyl nitrite, 5% (v/v) carbon monoxide and 40% (v/v) nitrogen was blown at a gas flow rate of 3.0 ml/min and at 50° C. After allowing of the gas mixture to pass through the system for 10 minutes, a mixed solution of diketene (255 mmol) and methanol (478 mmol) was added dropwise over 5 hours, during which reaction temperature was maintained at 50° C. with the same gas composition and the gas flow rate as the above. After completion of dropwise addition, blowing of the above gas mixture was further continued for one hour. After completion of the reaction, the reaction product was quantitatively analyzed by gas chromatography to have confirmed that 210 mmol of dimethyl acetone dicarboxylate was formed with a diketene conversion of 91%, and the selectivity based on diketene was 90.5%.

EXAMPLE 15

Into a glass autoclave having a gas inlet, a gas outlet and a liquid inlet was introduced acetonitrile (100 mmol) and palladium chloride (0.56 mmol), which was stirred under heating at 60° C. to prepare a homogeneous solution. To the autoclave, further introduced was a gas mixture of 16% (v/v) carbon monoxide, 19% (v/v) methyl nitrite and 65% (v/v) nitrogen up to a pressure of 5 atm.(guage). Thereafter, gas was withdrawn from the gas outlet at a flow rate of 680 ml/min so as to make the pressure in the system maintained at 3 atm.(guage). After allowing the gas to pass for 10 minutes, a mixture of diketene (258 mmol) and methanol (258 mmol) was introduced over 3 hours, during which the gas was allowed to pass in the reaction system while maintaining pressure of 3 atm.(guage). The reaction temperature was 60° C. After completion of the reaction, the reaction product was quantitatively analyzed to have confirmed that 92 mmol of dimethyl acetone dicarboxylate was formed with a diketene conversion of 40%, and the selectivity based on diketene was 89%.

EXAMPLE 16

Into a glass autoclave having a gas inlet, a gas outlet and a liquid inlet was introduced palladium chloride (0.56 mmol), cupric chloride (0.28 mmol) and acetonitrile (100 mmol), which was stirred under heating at 60° C. To a homogeneous solution thus prepared, further introduced was a gas mixture of 17% (v/v) carbon monoxide, 14% (v/v) methyl nitrite and 69% (v/v) nitrogen to a pressure of 5 atm.(guage). Thereafter, gas was withdrawn from the gas outlet at a flow rate of 680 ml/min so as to make the pressure in the autoclave maintained at 3 atm.(guage). After allowing the gas to pass for 10 minutes, a mixture of diketene (93 mmol) and methanol (93 mmol) was added to the reaction mixture over 3 hours, during which reaction temperature was maintained at 60° C. with the same gas composition and the gas flow rate as the above. After completion of the reation, the reaction product was quantitatively analyzed to have confirmed that 69 mmol of dimethyl acetone dicarboxylate was formed with a diketene conversion of 95%, and the selectivity based on diketene was 78%. Space time yield was 53 g/lit.-hr.

What is claimed is:

1. A process for preparing an acetone dicarboxylic acid diester, which comprises reacting at a temperature of from $-10°$ C. to 250° C. diketene, carbon monoxide and a nitrous acid ester in the presence of a catalyst comprising
   (a) a palladium halide selected from the group consisting of palladium chloride, palladium bromide and palladium iodide, or
   (b) a complex of a palladium halide selected from the group consisting of complexes of the formulae (i) $PdX_2(L-CN)_2$, wherein X is a halogen atom and L is an alkyl group having 1 to 20 carbon atoms or a phenyl group, (ii) $M_2PdX_4$ wherein M is an alkali metal and X is a halogen atom, or (iii) $(PdCl_2(olefin))_n$ wherein said olefin has 2 to 20 carbon atoms, and n is 1 or 2.

2. The process according to claim 1, wherein the palladium halide is palladium chloride.

3. The process according to claim 1, wherein said catalyst is a complex of palladium halide which is $PdCl_2(C_6H_5CN)_2$ or $PdCl_2(CH_3CN)_2$.

4. The process according to claim 1, wherein the palladium halide or the complex thereof is at a concentration in the reaction system of 1 ppm to 5 wt.% calculated on the basis of palladium metal.

5. The process according to claim 1, wherein the nitrous acid ester is an ester of a saturated monohydric aliphatic alcohol having 1 to 8 carbon atoms, or of an alicyclic alcohol, with nitrous acid.

6. The process according to claim 5, wherein said alcohol is one selected from the group consisting of methanol, ethanol, n-(and iso-)propanol, n-(iso-, sec-, tert-)butanol, n-(and iso-)amyl alcohol, hexanol, octanol, cyclohexanol and methyl cyclohexanol.

7. The process according to claim 6, wherein said alcohol is methanol, ethanol or butanol.

8. The process according to claim 1, wherein said nitrous acid ester is in an amount of from 2 to 100 moles per mole of diketene.

9. The process according to claim 1, wherein said diketene is added to the reaction system in an amount of from 0.1 to 30 wt.%.

10. The process according to claim 1, wherein said reaction is carried out in the presence of alcohol selected from the group consisting of a saturated monohydric aliphatic alcohol having 1 to 8 carbon atoms and an alicyclic alcohol in an amount of 20 moles or less per mole of diketene.

11. The process according to claim 10, wherein said alcohol is one selected from the group consisting of methanol, ethanol, n-(and iso-)propanol, n-(iso-, sec-, tert-)butanol, n-(and iso-)amyl alcohol, hexanol, octanol, cyclohexanol and methyl cyclohexanol.

12. The process according to claim 11, wherein said alcohol is methanol or ethanol.

13. The process according to claim 1, wherein said carbon monoxide is maintained at a partial pressure of from 0.01 to 100 atm.

14. The process according to claim 1, wherein said reaction is carried out in a liquid phase reaction using a solvent selected from the group consisting of acetonitrile, propionitrile, benzonitrile, dioxane, tetrahydrofuran, diethylether, dibutylether, chlorobenzene, nitrobenzene, dimethylformamide, dimethyl sulfoxide, nitromethane and acetone.

15. The process according to claim 1, wherein said reaction is carried out in the presence of said catalyst together with an accelerator, said accelerator comprising a copper salt selected from the group consisting of cuprous chloride, cupric chloride, cupric nitrate, cuprous bromide and cupric bromide in an amount of from 0.1 to 10 moles per mole of the palladium halide.

16. The process according to claim 1, wherein
    said catalyst is selected from the group consisting of palladium chloride, palladium bromide, palladium iodide, $PdCl_2(C_6H_5CN)_2$ and $PdCl_2(CH_3CN)_2$, in a concentration in the reaction system of 1 ppm to 5 wt.% calculated on the basis of palladium metal;
    said nitrous acid ester is an ester of an alcohol selected from the group consisting of methanol, ethanol, n-(and iso-)propanol, n-(iso-, sec-, tert-)butanol, n-(and iso-)amyl alcohol, hexanol, octanol, cyclohexanol and methyl cyclohexanol, and said nitrous acid ester is in an amount of from 2 to 100 moles per mole of diketene;
    said diketene is added to the reaction system in an amount of from 0.1 to 30 wt.% and
    said carbon monoxide is maintained at a partial pressure of from 0.01 to 100 atm.

17. The process according to claim 16, wherein said reaction is carried out in a liquid phase reaction using a solvent selected from the group consisting of acetonitrile, propionitrile, benzonitrile, dioxane, tetrahydrofuran, diethylether, dibutylether, chlorobenzene, nitrobenzene, dimethylformamide, dimethyl sulfoxide, nitromethane and acetone.

18. The process according to claim 16, wherein said reaction is carried out in the presence of said catalyst together with an accelerator, said accelerator comprises a copper salt selected from the group consisting of cuprous chloride, cupric chloride, cupric nitrate, cuprous bromide and cupric bromide in an amount of from 0.1 to 10 moles per mole of the palladium halide.

19. The process according to claim 18, wherein said reaction is carried out in a liquid phase reaction using a solvent selected from the group consisting of acetonitrile, propionitrile, benzonitrile, dioxane, tetrahydrofuran, diethylether, dibutylether, chlorobenzene, nitrobenzene, dimethylformamide, dimethyl sulfoxide, nitromethane and acetone.

20. The process according to claim 19, wherein said nitrous acid ester is an ester of methanol, ethanol or butanol.

21. The process according to claim 20, wherein said reaction is carried out in the presence of methanol or ethanol in an amount of 20 moles or less per mole of diketene.

22. The process according to claim 19, wherein said reaction is carried out in the presence of an alcohol selected from the group consisting of methanol, ethanol, n-(and iso-)propanol, n-(iso-, sec-, tert-)butanol, n-(and iso-)amyl alcohol, hexanol, octanol, cyclohexanol and methyl cyclohexanol in an amount of 20 moles or less per mole of diketene.

* * * * *